United States Patent [19]

Yun et al.

[11] Patent Number: 5,066,369
[45] Date of Patent: Nov. 19, 1991

[54] PROCESS FOR PREPARING PARA-AMINOPHENOL

[75] Inventors: Kyung S. Yun; Byung W. Cho, both of Seoul, Rep. of Korea

[73] Assignee: Korea Institute of Science and Technology, Rep. of Korea

[21] Appl. No.: 460,625

[22] Filed: Jan. 3, 1990

[30] Foreign Application Priority Data

Sep. 6, 1989 [KR] Rep. of Korea ............... 12903/1989

[51] Int. Cl.$^5$ ................................................ C25C 3/00
[52] U.S. Cl. ........................................ 204/74; 204/78
[58] Field of Search ................................ 204/74, 78

[56] References Cited

U.S. PATENT DOCUMENTS

| | | | |
|---|---|---|---|
| 1,501,472 | 7/1924 | Thatcher | 204/74 |
| 1,536,419 | 5/1925 | Burwell | 204/74 |
| 2,925,371 | 2/1960 | Van Winckel et al. | 204/74 |
| 2,998,450 | 8/1961 | Wilbert et al. | 204/74 |
| 3,338,806 | 8/1967 | Harwood | 204/74 |
| 3,645,864 | 2/1972 | Lawson et al. | 204/74 |
| 4,386,987 | 6/1983 | Covitch et al. | 204/98 |
| 4,445,985 | 5/1984 | Korach | 204/78 |
| 4,584,070 | 4/1986 | Delue et al. | 204/74 |

Primary Examiner—John F. Niebling
Assistant Examiner—Steven P. Marquis
Attorney, Agent, or Firm—Birch, Stewart, Kolasch & Birch

[57] ABSTRACT

A process for preparing para-aminophenol from nitrobenzene by utilizing electrochemical synthesizing method in high yield for dissolution or dispersion of nitrobenzene in electrolytic bath in which working electrodes are constituted with multi-rotating disk electrode having a plurality of disk electrode and solid polymer electrolyte electrode.

8 Claims, 2 Drawing Sheets

PARA-AMINOPHENOL

PROCESS FOR PREPARING PARA-AMINOPHENOL

BACKGROUND OF THE INVENTION

The present invention relates to a process for preparing para-aminophenol, more particularly to a process for preparing para-aminophenol from nitrobenzene by utilizing electrochemical synthesizing method without using either surfactant or any special solvent for dissolution or dispersion of nitrobenzene within electrolytic bath in which working electrodes are consisted of multi-rotating disk electrode (hereinafter refered to as multi-RDE) and solid polymer electrolyte (SPE) electrode.

For the conventional general process for preparing para-aminophenol, it can be mentioned a chemical method in which para-nitrophenol or nitrobenzene is hydrogenated in the present of catalyst. However, such chemical method is not recommendable since the reaction yield thereof is relatively low and moreover, the catalysts used therein are expensive noble metals such as platinum, etc.

To develop a new form of process for preparing para-aminophenol capable of overcoming aforementioned disadvantages in reaction yield and manufacturing cost, recent studies are concentrated on electrochemical synthesizing method (hereinafter referred to "electrolytic synthesizing method") and as its typical example, U.S. Pat. No. 3,338,806 can be mentioned.

Above patent relates to a method for producing para-aminophenol by electrochemically reducing nitrobenzene in electrolyte mixed with ethanol and sulfuric acid wherein since there are produced much undesirable reaction products such as aniline or azoxy benzene, not only reaction yield is low as about 62%, but also having problem that ethanol the solvent should be recovered. Further, although there has been known another electrolytic synthesizing method using 1-propanol as solvent instead of said ethanol, the reaction yield in high density nitrobenzene solution is poor as about 67%, and also having problem in that 1-propanol should be recovered in similar way as in case of the ethanol solvent.

On the other hand, according to the U.S. Pat. No. 4,584,070, as an expedient for eliminating the necessity of solvent recover problem in said manufacturing method, a method is disclosed which disperses surfactant (trialkylamine-N-oxide) simultaneously with forming separate third compartment between positive compartment and negative compartment of electrolytic bath whereby decreasing or preventing diffusion of oxygen produced in positive compartment into negative compartment while removing oxygen dissolved within negative compartment whereby suppressing the producing of azoxybenzene, a unnecessary reaction product.

However, according to the above patent, since the surfactant used in relatively large amount is expensive, and separate third compartment has to be provided within the interior of electrolytic bath, furnishing cost of electrolytic bath becomes increased, and since electrolytic voltage is raised, manufacturing cost is generally raised, on the other hand, as mercury among amalgamated metal electrode used for nagative electrode is dissolved into negative electrode solution, and contaminating reaction products and causing mercury pollution of solution, problems of contamination of environment by mercury as well as reduction of reaction yield according to the speeding up of aging of electrode are appeared.

Thus, in producing para-aminophenol from nitrobenzene by utilizing electrolytic synthesis, since said problem that negative electrode serves as very important factor, there is disadvantage that copper electrode, graphite electrode, and bismuth-coated copper electrode which are used as negative electrode other than amalgamated metal electrode also exhibit electrode dissolution phenomenon in case of reaction yield being high, on the contrary, in case of being extremely stable, reaction yield is low. [J. Jayaraman, K. S. Udupa and H. V. K. Udupa, SAEST, 12, 143 (1977)].

On the other hand, in order to raise the reaction yield, as method for utilizing catalyst and not dependent on improvement of electrode material, a method for scheming the increase of reaction yield by catalytic operation by pouring medium of tin ion within solution is known, however, this method is evaluated such that although reaction yield is raised a little, other problem such as necessity of recovering of medium is appeared, and consequently it is undesirable in economical view point. [H. C. Rance and J. M. Coulson, Electrochem. Acta, 14,283 (1969)].

Since nitrobenzene and reduced products of nitrobenzene are oxidized at positive electrode in case of electrolytic synthesis of para-aminophenol, it is essential to separate positive electrode compartment and negative electrode compartment by providing isolating membrane for the purpose of preventing this, and when considering the reaction mechanism of electrolytic synthesizing reaction of nitrobenzens into para-aminophenol, since hydrogen ion participates in the reaction and moreover, sulfuric acidic electrolyte is used, it is desirable to separate positive electrode compartment and negative electrode compartment by providing cation changing isolation membrane between positive electrode compartment and negative electrode compartment.

Meanwhile, even if being separated by cation-exchange isolation membrane, a part of nitrobenzene and reduced products of nitrobenzene become still migrate to positive electrode compartment, and this serves as a cause of reaction yield dropping.

Particularly, electrolytic synthesizing reaction mechanism of para-aminophenol is composed of producing reaction of intermediate, phenylhydroxylamine by electrochemical reducing reaction of nitrobenzene being of first step, and chemical transposing reaction of phenylhydroxyl amine being of intermediate product into para-aminophenol as second step. In such a two-step reaction mechanism, in case when chemical transposing reaction of second step is not carried out rapidly, phenyl hydroxylamine is reduced electrochemically around the electrode and being converted to anilin, a by-product, and in case when any oxygen exists within negative electrode compartment solution, phenyl hydroxylamine is converted to azoxybenzene and producing unnecessary reaction by-product whereby causing decrease of reaction yield.

Therefore, in order to raise the reaction yield in electrolytic synthesis of para-aminophenol, it is required to increase the reaction rate by promoting agitation of solution and also suppression of the migration of reaction material and reaction product into the other compartment.

SUMMARY OF THE INVENTION

Therefore, an object of the present invention is to provide a process for producing para-aminophenol by electrolytic synthesizing method for increasing surface area of electrode and promoting agitation of solution whereby increasing migration speed of nitrobenzene toward electrode, while promoting the migration of reaction product into solution whereby suppressing production of unnecessary by-product so that exhibiting high reaction yield.

Another object of the present invention is to provide a process for preparing para-aminophenol which carries out the reaction by dispersing nitrobenzene by means of promotion of agitating effect obtained by the use of multi-RDE with excluding the use of surfactant or solvent for dissolution or dispersion of nitrobenzene.

Further object of the present invention is to provide a process for preparing para-aminophenol in which reaction yield has been increased by preventing the migration of the reactant and product in solution of the negative electrode compartment into the positive electrode compartment and at the same time by suppressing the migration of oxygen generated in the positive electrode compartment into the negative electrode compartment by using SPE electrode together with said multi-RDE as working electrodes.

DETAILED DESCRIPTION OF THE PREFERRED EMBODIMENT

Figure 1:
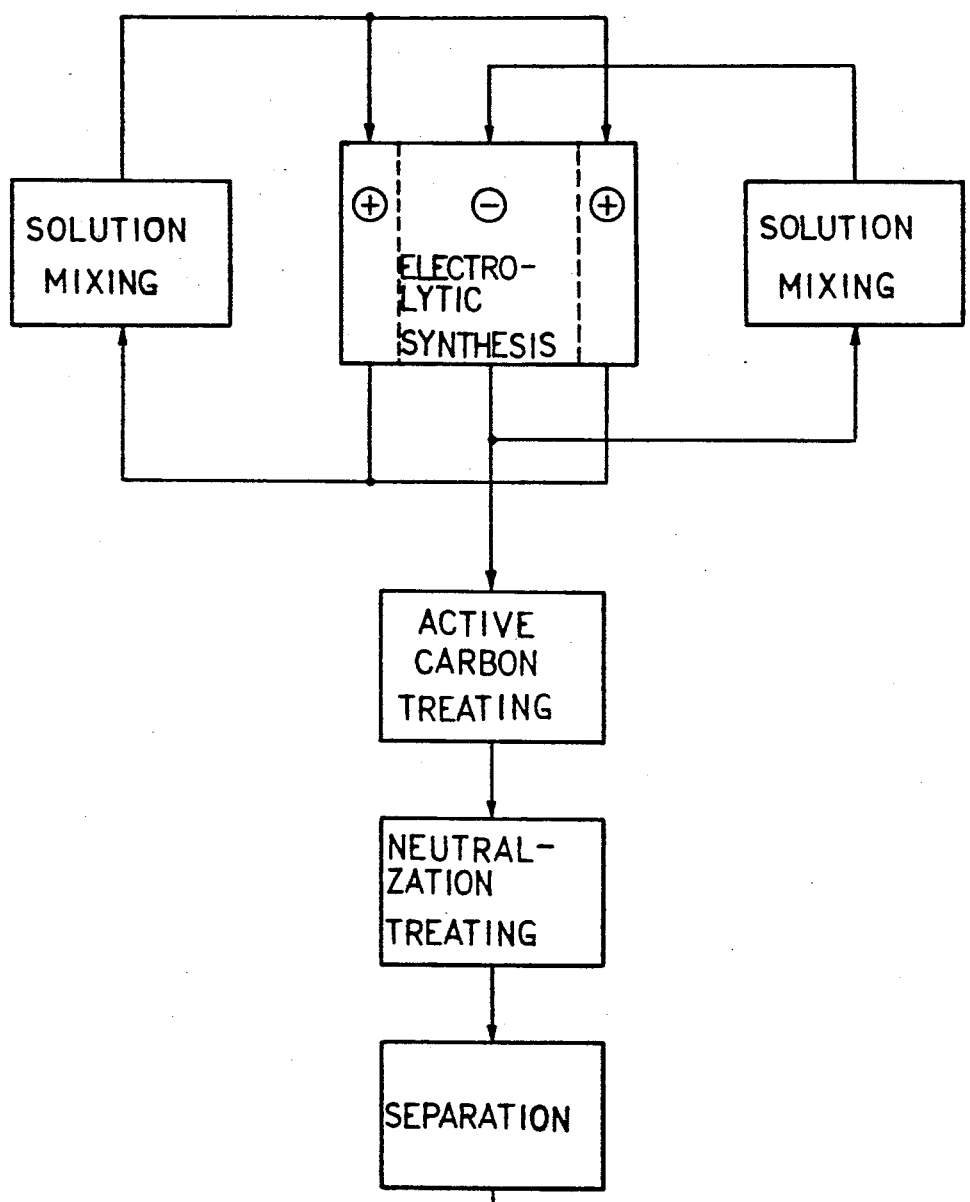
FIG. 1 is a schematic diagram for illustrating producing process of a preferred embodiment according to the present invention.

A process for preparing para-aminophenol by means of electrolytic synthesizing method of the present invention is comprised of a series of sequential process as "mixing of solution→electrolytic reaction→active carbon process→neutralizing process→separation" as shown in manufacturing process diagram of FIG. 1, wherein when explaining these respective process more in detail, it will be as following.

At first, in mixing process, nitrobenzene, sulfuric acid and water used for solution of negative electrode compartment are mixed, at the same time, sulfuric acid and water are mixed for solution of positive electrode compartment. Next, in a state that said mixed solutions are filled in negative electrode compartment and positive electrode compartment of electrolytic bath, respectively, nitrobenzene is reduced with negative electrode to produce para-aminophenol. The active carbon is added to electrolyzed and reacted mixture through electrolytic reaction, and the mixture is stirred at 90°-100° C. for several minutes and then eliminated organic material from the reaction mixture.

And then, in neutralization treating process, cooling the reaction mixture passed through active carbon treating process, and neutralizing within the range of pH 7.0-7.5 by using aqueous ammonia or sodium hydroxide with cooled condition to deposit para-aminophenol. Thereafter for final step, reaction mixture passed through neutralization treating process is sufficiently cooled, and then solid para-aminophenol is separated by centrifugal dehydroextractor, whereby manufacturing of para-aminophenol is finished.

Figure 2:
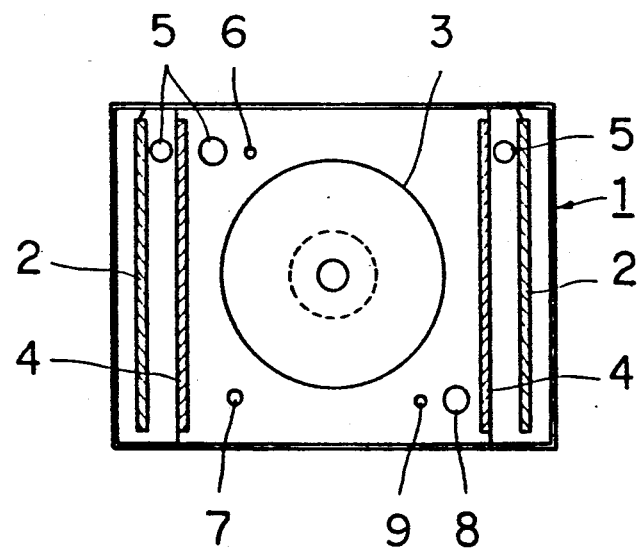
FIG. 2 is a plane view of electrolytic bath used for carrying out of the present invention.
Figure 3:
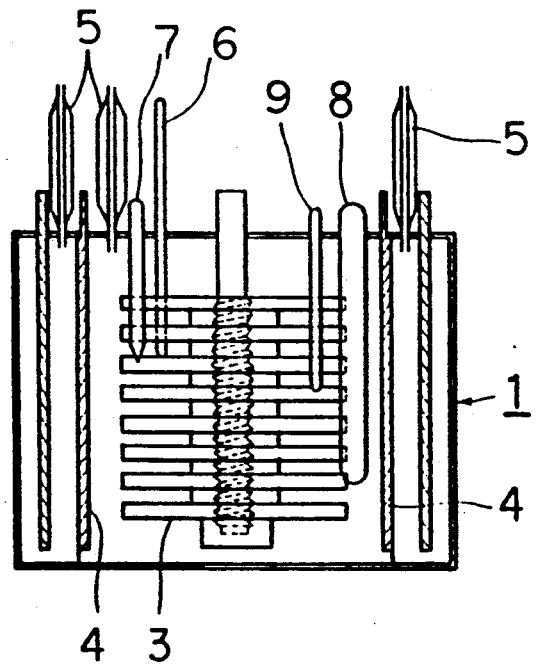
FIG. 3 is a vertical sectional view of FIG. 2.

According to the method of the present invention as aforementioned, it can be said that most important process is the process for synthesizing para-aminophenol electrochemically, and hereinafter, electrolytic reaction will be described in detail with reference to the accompanying FIGS. 2 and 3 which illustrate structure of electrolytic bath used for a preferred embodiment of the present invention.

The invention is constituted such that large electrodes 2 are respectively mounted at both sides within the interior of electrolytic bath 1, and multi-RDE 3 in which a plurality of large and small disk shaped RDE being formed by stacking alternately is formed at the center portion thereof, at the same time, SPE electrodes 4 are respectively formed between the large electrodes 2 and multi-RDE. In the drawings, reference numeral 5 is condenser, 6 is thermometer, 7 is reference electrode, 8 is heater, and 9 is thermometer.

Said multi-RDE is a rotational body formed by stacking with disc shaped RDE in multiple layers, in which thickness of diffusing layer becomes much thinner in accordance with the electrode itself being rotated whereby material migration speed of nitrobenzene toward electrode is increassed, at the same time, electrode surface area and agitating effect of solution are increased whereby reaction rate is increased.

Further, since diffusion of phenylhydroxylamine as an intermediate is promoted in accordance with the use of the multi-RDE, phenylhydroxylamine is no more reduced to aniline around the electrode, and directly converted to para-aminophenol, whereby the yield can be increased.

Thus, it is desirable to use the multi-RDE in the electrochemical reaction (for example, electrolytic synthesis of benzidine, dianicidine etc.) in which reaction rate and reaction yield are varied depending upon the material migration speed of reactant toward electrode and material migration speed of product into the solution.

Furthermore, as explained previously, in conventional process of the preparation of para-aminophenol by means of electrolytic synthesizing method, solvent or surfactant is used for the dissolution or dispersion of nitrobenzene, accordingly such conventional process has a problem that recovery of the solvent and consumption of high cost surfactant are unavoidable. However, by using the multi-RDE of the present invention, since agitating effect of solution is very good, nitrobenzene can be effectively electrolyzed and synthesized by dispersing without using any solvent or surfactant for dissolution or dispersion of nitrobenzene, therefore there is advantage that manufacturing cost can be saved.

On the other hand, as the electrode material of RDE, graphite electrode, copper electrode, graphite electrode coated with bismuth, amalgamated copper electrode, and copper electrode coated with bismuth which are not only possible to be made in sheet but also suitable for electrolytic synthesis, are used. Particularly, bismuth coating can be executed by means of several method such as chemical depoiting method, and electrical plating method etc., but the electrical plating method is the most economical and efficient method among these.

Electrical plating bath used for the electrical plating is classified generally into acidic bath and alkaline bath, and the acidic bath is widely used in general, wherein it is known that chloridizing bath among the acidic baths is most desirable in the light of cost, electric conducitivity, and safety property against temperature variation. [R. Walker and S. J. Snodk, Met. Finish., 78 (6), 79 (1980)].

Next, amalgamated copper electrode is made by means of submerging method and electrical plating method, and first the submerging method is a form of manufacturing the electrode by submerging copper electrode in dilute nitric acid and mercury alternately, while the electrical plating method in which the mercury forms amalgam together with copper by plating the mercury on the copper electrode in acidic solution dissolved with mercury ion.

In the present invention, the migration of either the nitrobenzene being a reactant among the solution of negative electrode compartment and its product toward the positive electrode compartment is prevented by simultaneously using said RDE together with SPE electrode as working electrode of electrolytic bath, at the same time, on the contrary, the migration of oxygen produced at the positive electrode compartment toward the negative electrode compartment is prevented, whereby the changing of phenylhydroxylic acid amine being an intermediate into azoxybezene, so that the yield is increased.

On the other hand, the electrolytic synthesis can be executed under the low electrolytic voltage by using only the SPE electrode in a state that using of the RDE is excluded, however in such case, since the intermediate product is rapidly released away from the electrode and chemical transposing reaction should be executed within solution, agitation of solution should be executed, wherein when agitation of solution is not executed, reaction yield becomes depreciated.

Generally, in organic electrolytic synthesis, selection of supporting electrolyte and solvent is considerably difficult problem, and seperating process of the desired product from the reacted mixture is also difficult, therefore recently, a research with respect to the electrolytic synthesizing method utilizing the SPE electrode has been actively developed as a scheme for solving such problems.

The SPE electrode is a combined electrode of a form combined with electronically conductive material such as metals, and as the combining method of electronically conductive material, chemical depositing method, physical depositing method, and non-electrolytic plating method are used among which non-electrolytic plating method is most econimical and efficient.

Particularly, permeating method is most widely utilized even among the various non-electrolytic plating method, wherein the permeating method means a method that solution of reducing agent (as an example: aqueous solution of hydrzaine) is put into one side of ion exchange membrane, and solution contained with metal ion desired to deposit is put into another side, and said reducing agent is passed through the SPE and then metal ion is reduced on opposite surface, whereby the metal ion is deposited on the SPE surface.

As the reducing agent, hypophosphate, hydrazine and the like can be used, and as the metal, platinum, nickel, copper, lead, bismuth and the like can be used.

The SPE electrode used in the present invention is SPE bismuth electrode which is suitable for electrolyzing and synthesizing para-aminophenol from nitrobenzene, and SPE bismuth electrode which is electrically plated with bismuth to the SPE copper electrode, and the like.

In the electrolytic synthesis of the present invention, reaction yield and reaction rate are affected by the electrolyzing condition such as electrolytic temperature, concentration of sulfuric acid, concentration of nitrobenzene, current density, and material property of negative electrode and positive electrode, wherein optimum conditions of these respective electrolyzing conditions are as follows.

At first, the higher the electrolytic temperature the faster the chemical transposing reaction of intermediate and as the electrolytic current becomes increased, the higher the electrolytic temperature, the more the reaction yield and reaction rate become increased, wherein desirable electrolytic temperature is 80°-95° C.

Next, concentration of sulfuric acid affects the reaction yield and reaction rate, wherein desirable concentration of sulfuric acid is 1.5-3.0M.

Concentration of nitrobenzene mainly affects the reaction yield, wherein the suitable concentration of nitrobenzene is 0.5-2.0M.

Current density represents the reaction rate and although there is an aspect that productivity is increased in reponse to the current density being increased, on the contrary, adverse effect that electrolytic voltage being raised and the slight decrease of reaction yield is observed, wherein the range of desirable current density of the multi-RDE is 20-200 mA/cm$^2$, and about 1/5-1/100 of the current density of the multi-RDE is sufficient for the SPE electrode, but optimum current density is varied depending upon the characteristic of electrolytic synthesis and the condition of reaction.

Rotational speed of the multi-RDE can be decreased as larger the diameter of disk electrode, the less the rotational speed, wherein the range of desirable rotational speed is 300-3600 rpm.

For the material of positive electrode (anode), lead-silver alloy electrode and dimensionally stable anode (DSA: Ti/IrO$_2$) which being stable in sulfuric acid are suitable.

And, by measuring the potential of the negative electrode relative to the reference electrode, it is possible to determine whether the electrolytic reaction is finished or not. In case when the electrolytic reaction is finished, the potential of the negative electrode is suddenly increased to negative (−) direction and reached a predetermined potential. For the reference electrode used at this moment, saturated calomel electrode (SCE) is disirable.

Hereafter, several examples are offered for producing para-aminophenol from nitrobenzene by using electrolytic synthesis method according to the present invention.

EXAMPLE 1

By using 2M sulfuric acid +1M nitrobenzene for the solution of negative electrode compartment without solvent or surfactant and by using 2M sulfuric acid for the solution of positive electrode compartment, electrolytic synthesis was carried out with graphite RDE negative electrode and Pb-Ag positive electrode at 90° C. under 50 mA/cm$^2$. Electrolysis was finished at the time when the potential of negative electrode was suddenly increased. After electrolysis, the solution was analyzed, and the reaction yield of para-aminophenol was 79%, and anilin was 19%, azoxybenze was 2%, and electrolytic voltage was 4.0 V.

EXAMPLE 2

Condition of solution and the positive electrode were same as example 1, and graphite RDE and SPE copper-bismuth electrode were used for the negative electrode, wherein the electrolytic synthesis was carried out with 45 mA/cm$^2$ of current density of SPE copper-bismuth electrode. The electrolysis was finished at the time when the potential of the graphite RDE was suddenly increased. The reaction yield of para-aminophenol was 85%, and aniline was 15%, azoxybenzene was almost not appeared. The electrolytic voltage was 3.7 V.

EXAMPLE 3

Condition of solution and the condition of positive electrode and negative electrode were same as example 2, and the electrolytic synthesis was carried out by setting the current density of the graphite RDE and the SPE copper-bismuth electrode respectively to 100 mA/cm$^2$ and 5 mA/cm$^2$. The electrolysis was finished at the time when the potential of the SPE electrode was suddenly increased, and reaction yield was such that para-aminophenol 83%, and aniline 17%. The electrolytic voltage was 5.0 V.

EXAMPLE 4

Condition of solution and the positive electrode were same as example 1, and the electrolytic synthesis was carried out in the state of the solution being agitated under the current density of 50 mA/cm$^2$ by using only the SPE copper-bismuth electrode for the negative electrode. The electrolysis was finished completely at the time when the potential of SPE electrode was suddenly increased, and the reaction yield of para-aminophenol was 75%, and aniline was 25%. And the electrolytic voltage was 3.5 V.

What is claimed is:

1. A process for preparing para-aminophenol from nitrobenzene comprising the step of:
    electrolytically synthesizing the solution of negative electrode compartment having sulfuric acid of 1.5–3.0M and nitrobenzene of 0.5–2.0M with working electrodes of solid polymer electrolyte electrode and multi-rotating disk electrode having a plurality of disk electrodes.

2. The process for preparing para-aminophenol according to claim 1, wherein said multi-rotating disk electrode is a material selected from the group consisting of graphite, copper, bismuth coated graphite, amalgamated copper and bismuth coated copper.

3. The process for preparing para-aminophenol according to claim 1, wherein said solid polymer electrolyte electrode is a material selected from the group consisting of solid polymer electrolyte copper-bismuth electrode, solid polymer electrolyte copper electrode and solid polymer electrolyte bismuth electrode.

4. The process for preparing para-aminophenol according to claim 1, wherein current density of said multi-rotating disk electrode is 20–200 mA/cm$^2$ and current density of said solid polymer electrolyte electrode is 1/5–1/100 of the multi-rotating disk electrode current density.

5. The process for preparing para-aminophenol according to claim 1, wherein said electrolytic temperature is 80°–95° C.

6. The process for preparing para-aminophenol according to claim 1, wherein rotational speed of said multi-rotating disk electrode is 300–3600 rpm.

7. The process for preparing para-aminophenol according to claim 1, wherein Pb-Ag or Ti/IrO$_2$ is used for said positive electrode.

8. The process for preparing para-aminophenol according to claim 1, wherein completion of said electrolysis is determined from increase of potential of negative electrode relative to a reference electrode.

* * * * *